US00PP34722P2

(12) United States Plant Patent
Espin

(10) Patent No.: US PP34,722 P2
(45) Date of Patent: Nov. 8, 2022

(54) GRAPEVINE PLANT NAMED 'GENSEL 1'

(50) Latin Name: *Vitis vinifera*
Varietal Denomination: GENSEL 1

(71) Applicant: Special New Fruit Licensing Mediterráneo S.L. (SNFL Mediterráneo S.L.), Murcia (ES)

(72) Inventor: Juan Carreño Espin, Murcia (ES)

(73) Assignee: SPECIAL NEW FRUIT LICENSING MEDITERRÁNEO S.L. (SNFL MEDITERRÁNEO S.L.), Murcia (ES)

( * ) Notice: Subject to any disclaimer, the term of this patent is extended or adjusted under 35 U.S.C. 154(b) by 0 days.

(21) Appl. No.: 17/576,262

(22) Filed: Jan. 14, 2022

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205, 206, 207
See application file for complete search history.

(56) References Cited

U.S. PATENT DOCUMENTS

| | | |
|---|---|---|
| PP17,504 P3 | 3/2007 | Maranto |
| PP22,125 P2 | 9/2011 | Van Kleinwee |
| PP33,356 P2 | 8/2021 | Martinez |

OTHER PUBLICATIONS

U.S. Appl. No. 17/576,280, filed Jan. 14, 2022, Espin.
U.S. Appl. No. 17/576,287, filed Jan. 14, 2022, Espin.

*Primary Examiner* — Susan McCormick Ewoldt
(74) *Attorney, Agent, or Firm* — Dentons LLP

(57) ABSTRACT

'GENSEL 1' is a new and distinct grapevine plant with novel characteristics that include good fertility and naturally loose bunches, nice and well-structured. The berries produced by 'GENSEL 1' are white and seedless with a crisp texture and neutral flavor and no detectable seed traces. The berries produced by 'GENSEL 1' are large, weighing 6-7 g/berry on average, and harvested in early September in Murcia Region (Spain).

1 Drawing Sheet

Latin name of the genus and species of the plant claimed: *Vitis vinifera.*

Cultivar denomination: 'GENSEL 1'.

BACKGROUND OF THE INVENTION

The present invention relates to a new distinct variety of seedless grapevine named 'GENSEL 1'. The new variety originated from a hybridization performed in Murcia, Spain during 2015 between '03-434-17' (U.S. Plant Pat. No. 33,356), as the pollen parent, and '9-704' (U.S. Plant Pat. No. 23,125), as the seed parent. Abortive seed traces were embryo cultured and the resulting plant was planted in an evaluation block during 2016. The first evaluation of the fruit produced by 'GENSEL 1' was performed during 2017. 'GENSEL 1' was first asexually propagated by field grafting dormant hardwood scions to 1103 Paulsen Rootstock (not patented) in 2018 in Murcia, Spain. Fruit from the resulting four grafted 'GENSEL 1' vines was first harvested in 2019. All characteristics and distinctions remain true to form and are established and transmitted through succeeding propagations.

SUMMARY OF THE INVENTION

The following are the most outstanding and distinguishing characteristics of 'GENSEL 1'. 'GENSEL 1' produces large, white (2.5GY6/8), seedless berries that are harvested in September, in Murcia-Spain and weigh on average 6-7 g/berry.

'GENSEL 1' is believed to be most similar to 'Blanc Seedless' (U.S. Plant Pat. No. 17,504 P3) but differs in maturity. Specifically, 'GENSEL 1' matures at least one week later than 'Blanc Seedless' with a sweet and very good flavor and texture. 'GENSEL 1' produces berries with a cylindrical shape whereas 'Blanc Seedless' produces berries with an ellipsoidal elongated shape. The new variety, 'GENSEL 1', has a higher fertility rate than 'Blanc Seedless' (1.2 v. 0.7).

'GENSEL 1' can be distinguished from its male parent, '03-434-17', in that 'GENSEL 1' clusters are less heavy than '03-434-17' clusters (average 650 g v. 800 g) and the average weight of 'GENSEL 1' berries is also smaller than '03-434-17' berries (average 9 g v. 6.2 g). The berries of 'GENSEL 1' have cylindrical shape while the berries of '03-434-17' are circular ellipsoid. Additionally, the variety 'GENSEL 1' has a higher fertility rate than '03-434-17' (1.2 v. 0.8).

'GENSEL 1' can be distinguished from its female parent, '9-704', in that the new cultivar produces white-coloured grapes while '9-704' produces red grapes. The berries of 'GENSEL 1' have a cylindrical shape whereas the berries of '9-704' have an oval shape. The harvest time of 'GENSEL 1' is two weeks before than the harvest time of '9-704'.

'GENSEL 1' is harvested in early September in Murcia, Spain, which is earlier than September-October harvest period of '03-434-17' and '9-704'.

BRIEF DESCRIPTION OF THE DRAWING

FIG. 1 Shows the form, foliage, and fruit of a 4-year-old 'GENSEL 1' vine grown in the field at Murcia, Spain. The colors shown are as true as can be reasonably obtained by conventional photographic procedures.

DETAILED BOTANICAL DESCRIPTION

The following detailed description sets forth the distinctive characteristics of 'GENSEL 1'. The detailed description was obtained between March and November using 4-year-old plants grown in the field in Murcia, Spain. The color references are to the *Munsell Plant Tissue Color Book,* 2012 Edition by Munsell Color.

Classification:

*Family*.—Vitaceae.
*Botanical.—Vitis vinifera.*
*Common name*.—Grapevine.
*Cultivar name*.—'GENSEL 1'.

Plant:

*Plant habit and growth*.—Semi-erect.
*Age at maturity*.—4 years old.
*Size* (*at maturity*).—Height: 225 cm. Width: 300 cm.
*Vigor*.—Medium.
*Productivity*.—High; 120 pound/vine; 53,000 pound/acre (this includes all the bunches).
*Rootstock*.—Name of rootstock: 1103 Paulsen Rootstock (not patented). Age of rootstock at time of grafting: one year old.

Trunk:

*Size*.—Diameter: 4.5 cm.
*Shape*.—Straight, cylindrical.
*Surface texture*.—Smooth, straight grained with the outer layer easily removed.
*Bark color*.—Exterior: 7.5YR6/2. Interior: 2.5YR3/4.

Canes:

*Size*.—Diameter: 9 mm. Length: 180 cm.
*Surface texture*.—Mature cane: smooth. Immature cane: smooth and finely ribbed.
*Form* (*woody shoot cross section form*).—Circular; pith in center with diaphragm at nodes.
*Color*.—Mature: 5 months, 5GY6/6 (anthocyanins: 10R3/4). Immature: 4 weeks, 5GY6/8 (anthocyanins: 2.5YR3/4). Dorsal side of internodes: 5GY6/6. Ventral side of internodes: 5GY6/6. Dorsal side of nodes: 5GY6/6. Ventral side of nodes: 5GY6/6.
*Internode length* (*upper mature sun cane*).—13 cm.
*Internode width* (*upper mature sun cane*).—7.6 mm.
*Node width*.—12.65 mm.

Bud:

*Bud description*.—Winter bud: rounded, pointed, 5YR4/4. Green bud: rounded, pointed, 5GY6/6.
*Time of bud burst*.—3 March.
*Time of bud leaf burst*.—8 March.

Tendrils:

*Form*.—Mostly trifid.
*Size*.—Medium.
*Length*.—23.5 cm.
*Diameter*.—2.3 mm.
*Texture and distribution of tendril at each node beginning at base*.—Smooth, discontinuous, 0000000001001010010010010 0101 (0 means no tendril at that node and 1 means there is tendril at the node).
*Color*.—Mature: 4 weeks, 5GY7/8. Immature: 10 days, 5GY7/8.
*Anthocynanin*.—Mature: absent. Immature: absent.

Growing tips (young shoot):

*Pubescence*.—Present. Low density of prostrate hairs on the shoot tip.
*Color*.—5GY5/6.
*Anthocynanin*.—Absent.
*Shape*.—Fully open.
*Apex*.—Triangular.
*Form of tip*.—Fully open.
*Shoot attitude before tying*.—Semi-erect.

Leaves:

*Shape*.—Orbicular-reniform.
*Apex*.—Pointed.
*Base*.—Rounded.
*Number of lobes*.—5.
*Arrangement*.—The leaves are arranged in alternative and opposite pattern. So, under a phyllotaxy ½ pattern.
*Depth of upper lateral sinuses of mature leaves*.—Deep.
*Arrangement of lobes of upper lateral sinuses on mature leaves*.—Slightly overlapped.
*Margin*.—Irregular teeth.
*Length of teeth on margin*.—2 to 10 mm.
*Shape of teeth on margin*.—Both sides convex.
*Texture* (*mature leaf*).—Upper surface: smooth. Lower surface: smooth, glabrous; some pubescence at primary vein junctions.
*Size*.—Immature: Length: 10 days, 7 cm. Width: 10 days, 7 cm. Mature: Length: 4 weeks, 17 cm. Width: 4 weeks, 16.7 cm.
*Color*.—Immature leaf: Upper surface: 5GY4/6. Lower surface: 5GY5/6. Mature leaf: Upper surface: 7.5GY4/4. Lower surface: 5GY5/6. Autumn coloration: Upper surface: 2.5Y7/8. Lower surface: 2.5Y7/8.
*Venation*.—Pattern: palmate (veins on upper leaf are flat; veins on lower leaf are raised). Length of middle vein in mature leaves: 4.74 cm. Color: Upper surface: 2.5GY7/6. Lower surface: 2.5GY7/4.
*Petiolar sinus*.—Lyre shaped, slightly open.
*Petiole*.—Length: 10 cm. Diameter: 3 mm. Color: 5GY7/8.

Flowers:

*Average no. of petals*.—5 petals that form the calyptra.
*Size*.—Height 2.8 mm; diameter: 2.2 mm.
*Color*.—Upper surface: 5GY4/8. Lower surface: 5GY6/8.
*Arrangement*.—The petals are fused together as a cap at the tip (calyptra).
*Shape*.—A cap with 5 fused petals.
*Texture*.—Smooth.
*Calyx*.—Very reduced, dome-shaped, and formed by 5 sepals join together. Size: very small (not measured). Color: 5GY6/8. Texture: smooth.
*Pistil*.—Bottle-shaped whose ovary is septate and contains 4 ovules.
*Average no. of stamen*.—5 stamens.

Floral cluster:

*General description and location*.—Mostly $6^{th}$ and $8^{th}$; 5% without shoulders.
*Quantity of inflorescences per cluster*.—545.
*Size*.—Length: 15.5 cm. Width: 6 cm hanging; 8 cm shoulders spread.
*Peduncle*.—Length: 3.6 cm. Diameter: 0.35 mm. Color: 5GY6/8.
*Inflorescences*.—Hermaphroditic.

*Stamens*.—Straight, 2.2 mm.

*Anthers*.—Small, nondescript.

*Date of bloom*.—Start: 3 May, 50%: 5 May, 100%: 10 May.

*Pollen amount*.—Moderate.

*Calyptra*.—5 segments, complete separation.

*Calyptra color*.—5GY4/8.

Fruit:

*Time of year of commercial harvest and shipment*.—Sep. 12, 2021. Keeping quality: After 30 days at cold storage, there are slight symptoms of dehydration of the secondary stem and the pedicel. The berries keep their crispness and their color without defects.

*Cluster* (*primary bunches*).—Generally size: large (650 g). Length (without peduncle): 25 cm. Width: 14.3 cm hanging and 26 cm with shoulders spread. Density: medium. Peduncle length: 7 cm. Peduncle diameter: 5 mm. Peduncle color: 2.5GY6/6. Number of berries per cluster: 94. Berry: Size: medium (6.2 g). Diameter: 18.1 mm. Length: 28 mm. Shape: cylindrical. Uniformity: uniform. Brix content: 21.2° Brix. Tiritable acidity: 0.75. Skin color (without bloom):2.5GY6/8. Skin color (with bloom): 2.5GY6/6. Pedicel: Length: 7.7 mm. Diameter: 1.44 mm. Color: 2.5GY6/6. Strength of attachment to berry: strong.

*Cluster* (*secondary bunches*).—Generally size: small (190 g). Length (without peduncle): 10.8 cm. Width: 10 cm hanging and 14.7 cm with shoulders spread. Density: medium. Peduncle length: 4.8 cm. Peduncle diameter: 3.8 cm. Peduncle color: 5GY7/6. Number of berries per cluster: 29. Berry: Size: small (4.4 g). Diameter: 17.4 mm. Length: 22.4 mm. Shape: cylindrical. Uniformity: very uniform. Brix content: 20° Brix. Tiritable acidity: 0.78. Skin color (without bloom): 2.5GY6/8. Skin color (with bloom): 2.5GY6/6. Pedicel: Length: 5.6 mm. Diameter: 1.4 mm. Color: 5GY7/6. Strength of attachment to berry: strong.

Berry flesh:

*Color*.—5GY7/6.

*Juice, color*.—2.5GY8/4.

*Juice production*.—Very high (44.4%).

*Thickness of skin*.—Medium.

*Flavor*.—Neutral, a hint of apple.

*Fragrance*.—Neutral, fresh, herbaceous.

*Texture*.—Very crisp (57 shores, (shore A scale)).

*Seeds*.—Not detectable.

*Use*.—Table grape.

Disease and insect resistance: This cultivar is susceptible to the main diseases of its species, such as *Erysiphe necator, Plasmopara viticola, Botrytis cinerea, Daktulosphaira vitifoliae, Ceratitis capitata, Planococcus ficus, Planococcus citri, Empoasca vitis*.

What is claimed is:

1. A new and distinct variety of grapevine named 'GENSEL 1' as shown and described herein.

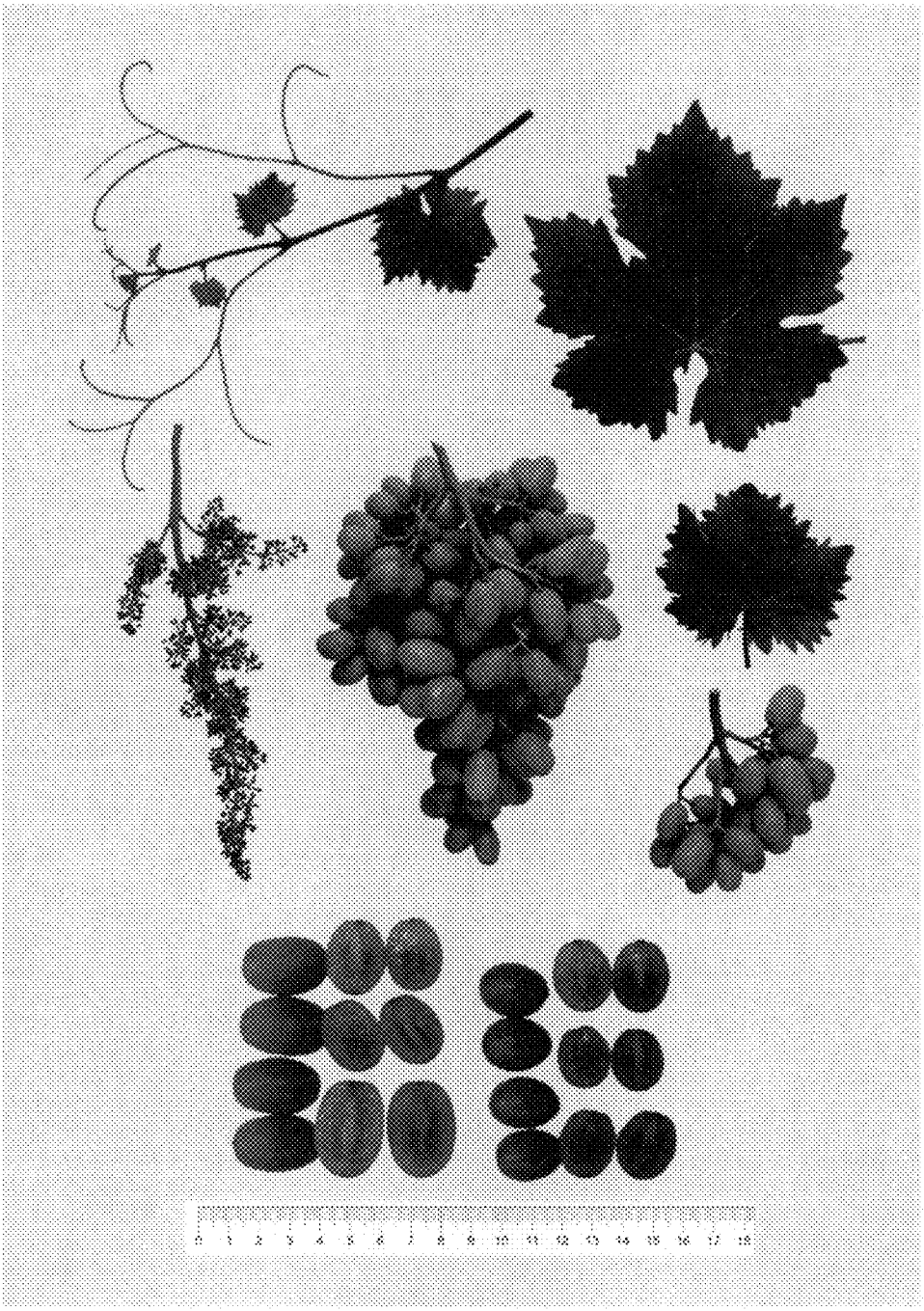

* * * * *